United States Patent
Sommerich

(10) Patent No.: US 7,429,241 B2
(45) Date of Patent: Sep. 30, 2008

(54) DURAL GRAFT AND METHOD OF PREPARING THE SAME

(75) Inventor: Robert E. Sommerich, Norton, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 292 days.

(21) Appl. No.: 11/238,717

(22) Filed: Sep. 29, 2005

(65) Prior Publication Data

US 2007/0073415 A1    Mar. 29, 2007

(51) Int. Cl.
*A61F 2/04*    (2006.01)

(52) U.S. Cl. ......................................... 600/36

(58) Field of Classification Search .................. 600/36; 128/897, 898

See application file for complete search history.

(56) References Cited

U.S. PATENT DOCUMENTS

| | | | |
|---|---|---|---|
| 2,465,357 A | 3/1949 | Correll | |
| 2,492,458 A | 12/1949 | Bering | |
| 3,157,524 A | 11/1964 | Artandi | |
| 3,364,200 A | 1/1968 | Aston et al. | |
| 3,520,402 A | 7/1970 | Nichols | |
| 3,632,361 A | 1/1972 | Battista | |
| 3,742,955 A | 7/1973 | Battista | |
| 3,800,792 A | 4/1974 | McKnight et al. | |
| 3,939,831 A | 2/1976 | Cioca et al. | |
| 4,006,220 A | 2/1977 | Gottieb | |
| 4,016,877 A | 4/1977 | Cruz, Jr. | |
| 4,066,083 A | 1/1978 | Ries | |
| 4,089,333 A | 5/1978 | Utsuo et al. | |
| 4,140,537 A | 2/1979 | Luck et al. | |
| 4,148,664 A | 4/1979 | Cruz, Jr. | |
| 4,185,011 A | 1/1980 | Eckmayer et al. | |

(Continued)

FOREIGN PATENT DOCUMENTS

EP     0667352     1/1995

(Continued)

OTHER PUBLICATIONS

Thompson et al., "Hemorrhage Associated with Silastic Dural Substitute", *J. of Neurology, Neurosurgery & Psychiatry*, 1994, 57: 646-648.

(Continued)

*Primary Examiner*—Samuel G Gilbert
(74) *Attorney, Agent, or Firm*—Nutter McClennen & Fish LLP

(57) ABSTRACT

A dural graft is provided having improved stiffness characteristics relative to conventional dural substitutes. The dural graft can be formed from a collagen material having a stiffness between about 0.1 pounds per inch (lb./in.) and 0.25 lb./in. Relative to the collagen material forming conventional dural graft substitutes, the decreased stiffness of the collagen material of the present dural graft can provide the graft with a relatively improved or increased pliability. As a result of the increased pliability, the dural graft can sufficiently conform to a curvature of a tissue surface to which it is applied, such as the curved surface of a meningeal membrane. The reduced stiffness of the collagen material can also provide for a relatively improved or increased flexibility or elasticity of the dural graft. The increased flexibility of the dural graft minimizes tearing of the graft when handled or manipulated during an implantation procedure.

5 Claims, 4 Drawing Sheets

U.S. PATENT DOCUMENTS

| | | | |
|---|---|---|---|
| 4,215,200 | A | 7/1980 | Miyata et al. |
| 4,233,360 | A | 11/1980 | Luck et al. |
| 4,238,480 | A | 12/1980 | Sawyer |
| 4,271,070 | A | 6/1981 | Miyata et al. |
| 4,294,241 | A | 10/1981 | Miyata |
| 4,404,033 | A | 9/1983 | Steffan |
| 4,404,970 | A | 9/1983 | Sawyer |
| 4,407,787 | A | 10/1983 | Stemberger |
| 4,412,947 | A | 11/1983 | Cioca |
| 4,522,753 | A | 6/1985 | Yannas et al. |
| 4,578,067 | A | 3/1986 | Cruz, Jr. |
| 4,600,533 | A | 7/1986 | Chu |
| 4,606,910 | A | 8/1986 | Sawyer |
| 4,655,980 | A | 4/1987 | Chu |
| 4,689,399 | A | 8/1987 | Chu |
| 4,725,671 | A | 2/1988 | Chu et al. |
| 4,738,849 | A | 4/1988 | Sawyer |
| 4,798,800 | A | 1/1989 | Timpl et al. |
| 4,837,285 | A | 6/1989 | Berg et al. |
| 4,947,840 | A | 8/1990 | Yannas et al. |
| 4,948,540 | A | 8/1990 | Nigam |
| 4,970,298 | A | 11/1990 | Silver et al. |
| 5,019,087 | A | 5/1991 | Nichols |
| 5,028,695 | A | 7/1991 | Eckmayer et al. |
| 5,071,878 | A | 12/1991 | Herschler |
| 5,110,604 | A | 5/1992 | Chu et al. |
| 5,171,574 | A * | 12/1992 | Kuberasampath et al. ... 424/423 |
| 5,201,745 | A | 4/1993 | Tayot et al. |
| 5,209,776 | A * | 5/1993 | Bass et al. ............... 106/124.1 |
| 5,215,904 | A | 6/1993 | Gould et al. |
| 5,227,301 | A | 7/1993 | Turner et al. |
| 5,412,076 | A | 5/1995 | Gagnieu |
| 5,512,301 | A | 4/1996 | Song et al. |
| 5,567,806 | A | 10/1996 | Abdul-Malak et al. |
| 5,580,923 | A | 12/1996 | Yeung et al. |
| 5,667,839 | A | 9/1997 | Berg |
| 5,677,839 | A | 10/1997 | Kondo |
| 5,895,412 | A * | 4/1999 | Tucker ....................... 606/215 |
| 5,931,800 | A | 8/1999 | Rasmussen et al. |
| 5,997,895 | A | 12/1999 | Narotam et al. |
| 6,149,609 | A * | 11/2000 | Lieberman et al. .......... 600/587 |
| 6,270,793 | B1 | 8/2001 | Van Dyke et al. |
| 6,274,155 | B1 | 8/2001 | Van Dyke et al. |
| 6,361,551 | B1 | 3/2002 | Torgerson et al. |
| 6,454,787 | B1 | 9/2002 | Maddalo et al. |
| 6,461,628 | B1 | 10/2002 | Blanchard et al. |
| 2003/0220334 | A1 | 11/2003 | Wender et al. |
| 2004/0028738 | A1 | 2/2004 | Huang et al. |

FOREIGN PATENT DOCUMENTS

| | | |
|---|---|---|
| EP | 0 440 198 B1 | 11/1995 |
| EP | 0742018 | 11/1996 |
| EP | 0 877 761 B1 | 5/2001 |
| EP | 05250694.6 | 1/2006 |
| JP | 08041425 | 2/1996 |
| WO | WO 9420133 | 9/1994 |
| WO | WO 9625961 | 2/1996 |
| WO | WO 9617633 | 6/1996 |
| WO | WO 9640174 | 6/1996 |
| WO | WO 9728192 | 1/1997 |
| WO | WO9737694 | 4/1997 |
| WO | WO 9728193 | 8/1997 |
| WO | WO 99/13902 | 3/1999 |

OTHER PUBLICATIONS

Taylor et al., "Unconventional Transmissible Agents in Dura Matter: Significance for Iatrogenic Creutzfeldt-Jakob Disease", *Neuropathology & Applied Neurobiology*, 1996, 22: 259-260.

D.G. Kline, "Dural Replacement with Resorbable Collagen", *Arch Surg*, 1965 91: 924-929.

Doillon et al., "Transmission of Creutzfeldt-Jakob Disease by Handling of Dura Matter", *The Lancet*, 1993, 341: 123-124.

Janetta et al., "Formaldehyde-Treated Regenerated Collagen Film and Film-Laminate as a Substitute for Dura Mater", Proceedings of the 21st Annual Sessions of the Forum on Fundamental Surgical Problems, 51st Clinical Congress of the American College of Surgeons, Atlantic City, New Jersey, 1965, Surgical Forum, vol. XVI, pp. 435-437.

Collins et al., "Use of Collagen Film as Dural Substitute: Preliminary Animal Studies", *J. of Biomedical Material Research*, 1991, 25:267-276.

Doillon et al., "Chemical Inactivators as Sterilization Agents for Bovine Collagen Materials", National library of Medicine Medline Database, TBIS, 2003, Abstract, p. 3.

Dormont, D., "How to Limit the Spread of Creutzfeldt-Jakob Disease", National Library of Medicine Medline Database, TBIS, 2003, Abstract, p. 4.

Rohwer, R.G., "Analysis of Risk to Biomedical Products Developed from Animal Sources (with Special Emphases on the Spongiform Encephalopathy Agents, Scrapie and BSE)", National Library of Medicine Medline Database, TBIS, 2003, abstract, p. 5.

Safar, J. et al., "Thermal Stability and Conformational Transitions of Scrapie Amyloid (Prion) Protein Correlate with Infectivity", National Library of Medicine Medline Databse, TBIS, 2003, Abstract, p. 5.

Taylor, D.M., "Inactiviation of SE Agents", National Library of Medicine Medline Database TBIS, 2003, Abstract, p. 6.

Ernst & Race, "Comparative Analysis of Scrapie Agent Inactivation Methods", National Library of Medicine Medline Database, TBIS, 2003, Abstract, p. 6.

DiMartino et al., "Inactivation of the Scrapie Agent in a Scaled-down Procedure for the Purification of Gangliosides from Brain Tissue", National Library of Medicine Medline Database, TBIS, 2003, Abstract, p. 7.

Tateishi et al., "Practical Methods for chemical Inactivation of Creutzfeldt-Jakob Disease Pathogen", National Library of Medicine Medline Database, TBIS, 2003, Abstract, p. 7.

Taylor, D. M., "Inactivation of BSE Agent", National Library of Medicine Medline Database, TBIS, 2003, Abstract, p. 7.

Brown et al., "A Simple and Effective Method for Inactivating Virus Infectivity in Formalin-fixed Tissue Samples from Patients with Creutzfeldt-Jakob Disease", National Library of Medicine Medline Database, TBIS, 2003, Abstract, p. 8.

Dees et al., "Inactivation of the Scrapie Agent by Ultraviolet Irradiation in the Presence of Chlorpromazine", National Library of Medicine Medline Database, TBIS, 2003, Abstract, p. 9.

Cho, H. J., "Inactivation of the Scrapie Agent by Pronase", National Library of Medicine Medline Database, TBIS, 2003, Abstract, p. 10.

Brown et al., "Effect of Chemicals, Heat and Histopathologic Processing on High-Infectivity Hamster-Adapted Scrapie Viirus", National Library of Medicine Medline Database, TBIS, 2003, Abstract, p. 10.

Cox., "A Systematic Review of the Published Literature to Identify the Methods of Inactivation for Unconventional Agents of Transmissible Spongiform Encephalopathies", Medical Devices Agency, UK, 2001, pp. 1-13.

Archibald et al., "Long Term Maintenance of Axonal Regeneration in Primates Following Collagen Nerve Guide Repair of 2CMMedian Nerve Deficit", *Society for Neuroscience Abstracts*, 1992, vol. 18, Part1, Abstract.

Li, Shu-Tung, "Peripheral Nerve Repair with Collagen Conduits", *Clin. Materials*, 1992, 9:195-200.

Archibald et al., "A Collagen Based Nerve Guide Conduit for Peripheral Nerve Repair; An Electrophysiological Study of Nerve Regeneration in Rodents and Nonhuman Primates", *J. of Comparative Neurology*, 1991, 306: 685-696.

Archibald et al., "Monkey Median Nerve Repaired by Nerve Graft or Collagen Nerve Guide Tube", *J. of Neuroscience*, 1995, 15(5): 4109-4123.

Krarup et al., "Factors that Influence Peripheral Nerve Regeneration: An Electrophysiological Study of the Monkey Median Nerve", *Annals of Neurology*, 2002, 51: 69-81.

Madison et al.; "Factors Contributing to Preferential Motor Reinnervation in the Primate Peripheral Nervous System"; *J. of Neuroscience*, 1999, vol. 19 (24); 11007-11016.

* cited by examiner

DURAL GRAFT AND METHOD OF PREPARING THE SAME

FIELD OF THE INVENTION

The present invention relates to a dural graft and a method of preparing the same.

BACKGROUND OF THE INVENTION

The human brain and spinal cord are covered with meningeal membranes, the integrity of which is critical to the operation of the central nervous system. When the integrity of a person's meningeal membranes is intentionally or accidentally compromised, serious consequences may ensue, unless the membranes can be repaired. The meningeal membrane comprises three overlapping layers of tissue, which are in order from outside to inside, the dura mater (or dura), the arachnoid and the pia mater. Repairing damaged meningeal membranes has largely focused on implantable and/or resorbable constructs, known as dural substitutes, which are grafted to the damaged dura mater and are designed to replace and/or regenerate the damaged tissue.

While dural substitutes are effective in covering and repairing damaged dura mater, the conventional dural substitutes can be relatively fragile. For example, conventional hydrated dural substitutes can be formed of a porous, sponge-like collagen structure. During handling or manipulation of these dural substitutes, the substitutes can be inadvertently pulled or placed under sufficient tension to create tears in the collagen structure, thereby destroying the dural substitute.

Accordingly, there remains a need for a dural substitute having improved stiffness characteristics that allows for handling of the dural substitute while minimizing the risk of tearing the substitute.

SUMMARY OF THE INVENTION

The present invention provides a dural substitute having improved stiffness characteristics relative to conventional dural substitutes. In one embodiment, a dural graft is provided having a size and shape suitable for placement to repair or replace a damaged meningeal membrane. The dural graft can be formed of a collagen material having a stiffness in a range of about 0.01 pounds per inch to 0.25 pounds per inch. In one embodiment, however, the collagen material can have a stiffness in a range of about 0.04 pounds per inch to 0.12 pounds per inch. The dural graft can include one or more biological agents such as an antibiotic, a growth factor, a hemostasis factor, an anti-adhesion agent, and an anti-cancer agent. The collagen material can be formed from a substantially fluid impermeable material.

In one embodiment, a dural graft material is provided having a first collagen layer having opposed surfaces and a second collagen layer disposed on at least a first surface of the first collagen layer. The second collagen layer can have a stiffness in a range of about 0.01 pounds per inch to 0.25 pounds per inch.

In another aspect, the present invention provides a method for manufacturing a dural graft substitute that includes delivering energy to a collagen material at a power level and for a period of time sufficient to reduce a stiffness of the collagen material to a stiffness in a range of about 0.01 pounds per inch to 0.25 pounds per inch. The energy can include a microwave energy applied at a power of about 700 Watts for a duration of about 30 seconds to reduce the stiffness of the collagen material. The microwave energy can also be applied at a power of about 700 Watts for a duration of about 60 seconds. Other types of energy can be delivered to the collagen material to reduce the stiffness of the collagen material. For example, radiation energy or electron beam energy can be used to irradiate the collagen material to reduce the stiffness of the material.

BRIEF DESCRIPTION OF THE DRAWINGS

The invention can be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with features of other embodiments. Such modifications and variations are intended to be included within the scope of the present invention.

The present invention provides a dural graft suitable to repair or replace damaged meningeal membranes. In general, a dural graft can be formed from a collagen material having a stiffness between about 0.1 pounds per inch (lb./in.) and 0.25 lb./in. Relative to the collagen material forming conventional dural graft substitutes, the decreased stiffness of the collagen material of the present dural graft can provide the graft with a relatively improved or increased pliability. As a result of the increased pliability, the dural graft can sufficiently conform to a curvature of a tissue surface to which it is applied, such as the curved surface of a meningeal membrane. The reduced stiffness of the collagen material can also provide for a relatively improved or increased flexibility or elasticity of the dural graft. The increased flexibility of the dural graft minimizes tearing of the graft when handled or manipulated during an implantation procedure.

Figure 1:
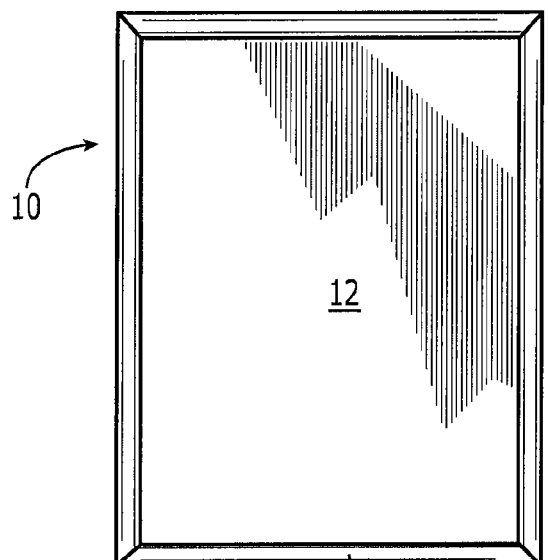
FIG. 1 illustrates a top view of a dural graft.
Figure 2:
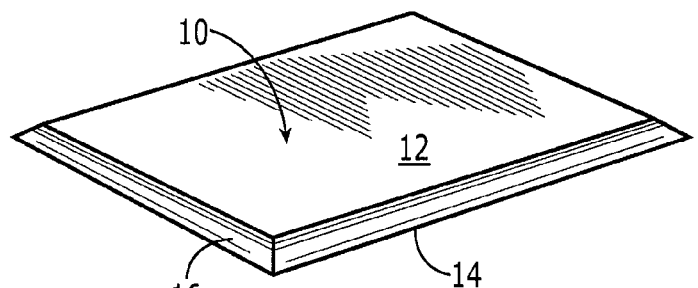
FIG. 2. illustrates a perspective view of the dural graft of FIG. 1.
Figure 3:
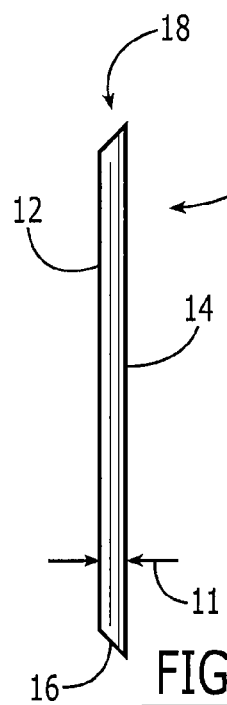
FIG. 3 illustrates a side view of the dural graft of FIG. 1.

FIGS. 1-3 illustrate an embodiment of a dural graft 10. The dural graft 10 can be formed of a collagen material having a desired shape, such as a generally rectangular geometry as shown, and having a desired thickness 11, such as a thickness 11 within the range of about 0.020 inches and 0.240 inches. In one embodiment, the dural graft 10 has a thickness in the range of about 0.120 inches and 0.129 inches. For example, the dural graft 10 can be formed having a top surface 12, a bottom surface 14 and peripheral edge 16. The edge 16 of the dural graft 10 defines the generally rectangular shape of the graft 10. In one embodiment, the edge 16 of the dural graft 10 can be chamfered to allow a smooth profile of the edge 16 when it is wetted in situ, as shown in FIGS. 1-3. The edge 16 can be chamfered at an angle 18 of approximately 30 to 75 degrees relative to the top surface 12. While the dural graft 10 is shown as having a generally rectangular geometry, one skilled in the art will appreciate that the dural graft 10 can be formed into other geometries as well. For example, the dural graft 10 can be formed into a circle, triangle, or other geometries. In one embodiment, the dural graft 10 can have The collagen material that forms the dural graft 10 can be produced according to the process described in U.S. patent application Ser. No. 10/955,835, filed Sep. 30, 2004 and entitled COLLAGEN AND METHOD OF PREPARING THE SAME, the contents of which are expressly incorporated herein by reference in their entirety. A summary of the process is provided below.

A collagen powder is mixed with purified water for a period of time sufficient to form a mixture. The ratio of collagen to purified water can be between approximately 0.4% to 5.0% w/w. The pH of the mixture is then adjusted to a pH level sufficient to substantially solubilize the collagen. A predetermined amount of the mixture is then placed into a container. The mixture is then formed into a collagen sheet by a lyophilizing process. The mixture could also be formed into a block, cylinder, or other desired shape, which will hereinafter be referred to collectively as a collagen sheet. The collagen sheet is then cross-linked. During the cross-linking, the collagen sheet is preferably exposed to a liquid or vapor form of a cross-linking agent, such as formaldehyde or glutaraldehyde. Thereafter, the collagen sheet can be ventilated if the cross-linking agent is vapor or relyophilized if it is liquid. The resulting collagen material has a plurality of pores wherein a majority of the pores (e.g., greater than approximately 80% of the pores) have a diameter of less than 10 μm.

Once the collagen material has been formed, the material has a particular stiffness. Generally, the stiffness of a material is defined as ratio of the displacement or stretching of the material relative to a change in load applied to the material (e.g., stiffness=change in load/displacement). The relationship between load and displacement for a material can be plotted on a Cartesian coordinate system (e.g., with displacement being a function of load) to produce a load-displacement curve. Generally, a slope of the curve representing the load-displacement relationship of the material relates to the stiffness for that material. Typically, the steeper the slope of the curve (e.g., the larger the slope value), the stiffer the material.

Figure 4:
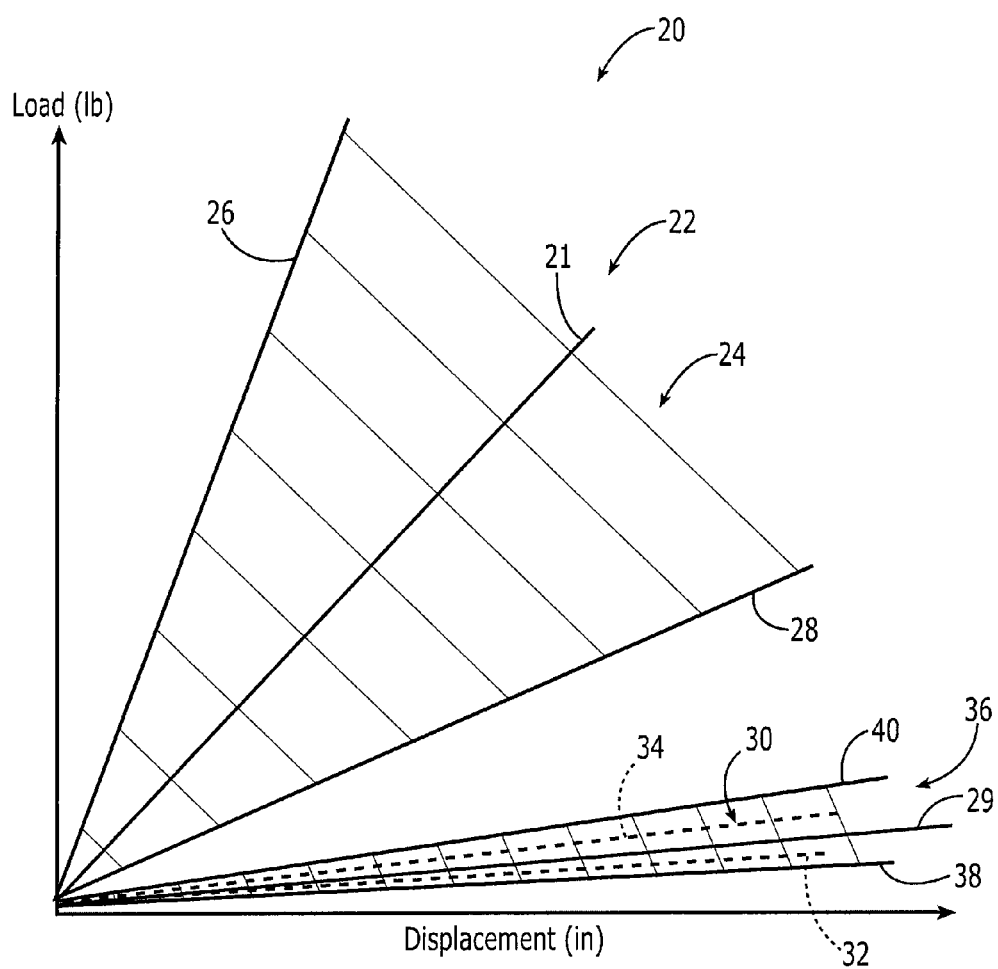
FIG. 4 is a graph showing stiffness ranges for conventional collagen devices and the dural graft of FIG. 1.

For example, FIG. 4 illustrates a graph 20 showing an average load-displacement relationship or curve 21 for a conventional collagen material (e.g., as formed in the process described above). In one embodiment, the average slope of the load-displacement curve 21 for conventional collagen materials is about 4.0 lb./in. As indicated above, the slope of the curve 21 relates to the stiffness of the collagen material. With the stiffness of the collagen material being about 4.0 lb./in., the collagen material can be considered as a relatively stiff material (e.g., as having a relatively high stiffness). As a result, grafts formed from such collagen materials can be considered as relatively inelastic in that minimal stretching of the graft when the graft is handled or manipulated can cause the graft to tear.

In one embodiment, the stiffness for a conventional collagen material can fall within a range 24 of values represented on the graph 20 by an upper threshold 26 and a lower threshold 28. The slopes of these thresholds 26, 28 represent the range of stiffness values for the conventional collagen materials. For example, in one embodiment the upper threshold 26 can represent a collagen material stiffness of approximately 7.30 lb./in. while the lower threshold 28 can represent a collagen material stiffness of approximately 0.60 lb./in. With the stiffness of the collagen material falling within such a range 24, the collagen material can be considered as a relatively stiff material (e.g., as having a relatively high stiffness).

In order to reduce the relative inelasticity and increase the pliability and flexibility of the collagen material, the stiffness of the collagen material forming the dural graft 10 can be reduced. For example, reduction of the stiffness below the lower threshold 28 of 0.60 lb./in. can and increase the pliability and flexibility of the collagen material. In one embodiment, to affect a reduction of the stiffness, energy can be applied to the collagen material.

In one embodiment, microwave energy can be used to reduce the stiffness of the collagen material. For example, the collagen material, which may be wetted or moist, can be placed in the vicinity of a microwave emitting device, such as within a microwave oven, and exposed to the microwave energy emitted by the device. As a result of such exposure, the microwave energy can change the material properties of the material and reduce the stiffness of the collagen material below the lower threshold 28 (e.g., approximately 0.60 lb./in.) as illustrated in FIG. 4. For example, FIG. 4 illustrates a load-displacement curve 29 representing the stiffness for a conventional collagen material exposed to a microwave energy of approximately 700 Watts. As illustrated, the stiffness of the collagen material is below the lower threshold 28. In one embodiment, the average stiffness for the collagen material exposed to the microwave energy source is about 0.09 lb./in.

One skilled in the art will appreciate that while microwave energy can be used to reduce the stiffness the collagen material, other energy forms can be used as well. In one embodiment, heat can be applied to the collagen material in a moist environment to reduce the stiffness of the material. By way of non-limiting example, the collagen material can be exposed to a heated fluid, such as heated water, or to heated steam. In another example, the collagen material can be exposed to an energy source, such as a heat lamp, in a moist environment. In such an embodiment, the collagen material can be wetted, moist, or dry. In another embodiment, other types of energies can be applied to the collagen material such as, for example, radiation energy from a radiation source or energy from an electron beam.

While the application of energy to the collagen material can decrease the stiffness of the material, other factors related to the energy application can affect the decrease in stiffness. In one embodiment, the power level of the energy applied to the collagen material and the duration of application of the energy can affect the reduction in stiffness of the collagen material. By way of non-limiting example, the following describes the stiffness changes in a collagen material after application of microwave energy for varying durations of time.

Collagen material taken from 11 inch×11 inch sheets was formed into substantially rectangular shaped sheets, each having a length of approximately 3 inches, a width of approximately 3 inches, and an average thickness of approximately 0.146 inches (e.g., within the range of approximately 0.12 inches and 0.19 inches). Nine of the collagen sheets were exposed to a microwave energy at a power or energy level of approximately 700 Watts for a duration of approximately 20 seconds and ten of the collagen sheets were exposed to a microwave energy at a power level of approximately 700 Watts for a duration of approximately 60 seconds. Tensile loads were applied to each of the sheets and the resulting displacements measured. The stiffness of each collagen sheet was then calculated from the corresponding load—displacement data and the stiffness range (e.g., average stiffness +/−standard deviation) for each group (e.g., 20 second group or 60 second group) was determined.

One skilled in the art will appreciate that the duration of exposure to energy and the power level of applied energy can vary depending on a number of factors, including the amount of material to be treated and the desired stiffness level. In addition, the type of energy used to treat the collagen material can also vary. For collagen materials treated according to the invention by exposure to microwave energy, the power level can be in the range of about 50 to 1200 Watts, and more preferably in the range of about 200 to 800 Watts. The material can be exposed to such microwave energy for a time period in the range of about 5 seconds to 180 seconds and more preferably for a period of time in the range of about 15 seconds to 60 seconds.

With respect to the above-reference example, FIG. 4 illustrates a first range of stiffness values 30 for the collagen material (e.g., as described above) exposed to the microwave energy for the duration of approximately 20 seconds. In one embodiment, as a result of such exposure, the collagen material can have a stiffness in a range of about 0.04 lb./in., as indicated by lower curve 32, and 0.12 lb./in, as indicated by upper curve 34. FIG. 4 also illustrates a second range of stiffness values 36 for the collagen material exposed to the microwave energy for the duration of approximately 60 seconds. In one embodiment, as a result of such exposure, the collagen material can have a stiffness in a range of about 0.01 lb./in., as indicated by lower curve 38, and 0.25 lb./in. as indicated by upper curve 40. In either case, exposure of the collagen material to a microwave energy at a substantially constant power level for a period of time (e.g., 20 seconds or 60 seconds) can decrease the stiffness of the collagen material.

In one embodiment, for a substantially constant power level, changing the duration of a collagen material's exposure to microwave energy can affect a decrease in the stiffness of the material. For example, increasing an amount to time that a collagen material is exposed to a microwave energy can further reduce the stiffness of the collagen material (e.g., below 0.01 lb./in). In another embodiment, either the power level, the duration of time, or a combination of both can be adjusted in order to affect the decrease in the stiffness of the collagen material. For example, in one embodiment, over a substantially constant duration of time, changing the power level of the energy applied to the collagen material can affect the decrease in the stiffness of the collagen material.

The above example also indicates that for collagen material formed into sheets having a particular dimension (e.g., a length of approximately 3 inches, a width of approximately 3 inches, and an average thickness of approximately 0.146 inches), application of microwave energy at a constant power level and for varying durations of time can reduce the stiffness of the collagen material to a particular level, as shown in FIG. 4. In one embodiment, for relatively larger or smaller amounts of collagen material, the power level and the duration of exposure can be adjusted to reduce the stiffness of the collagen material to the particular level (e.g., the power level of the energy source and the duration of exposure can be a function of the amount of collagen material used). For example, for a relatively larger amounts of collagen material, (e.g., relative to the amounts used in the above-described example), the power level of the energy source, the duration of exposure, or a combination of both, can be increased in order to reduce the stiffness of the collagen material to the stiffness range illustrated in FIG. 4. In another embodiment, the power level of the microwave energy can vary over a given period of time to reduce the stiffness of a collagen material. For example, the collagen material can be exposed to a linearly increasing, linearly decreasing, or cyclically changing power over a time interval.

While the application of energy to the collagen material can decrease the stiffness of the collagen material, the applied energy can also alter or adjust other properties of the material. In one embodiment, application of energy to the collagen material can adjust the fluid impermeability of the material. For example, collagen material has a substantially porous, sponge-like structure that, while resistant to the passage of fluid such as cerebrospinal spinal fluid (CSF), is not completely fluid impervious. When exposed to a microwave energy, the energy can cause the collagen material to shrink to approximately ⅓ of its original size (e.g., original volume) and can adjust the porous, sponge-like structure of the collagen material such that the material becomes less porous and more membrane-like (e.g., the collagen material takes on a membrane-like material "feel"). As a result of such physical changes, the microwave energy can reduce the ability for fluids to pass through the collagen material and can increase the fluid imperviousness of the material.

Returning to FIG. 1, while the dural graft 10 can be formed of a collagen material, the dural graft 10 can include other materials as well. In one embodiment, one or more biological or biologically active agents can be incorporated within the dural graft 10. For example, the biological agents can include antibiotics, growth factors, hemostasis factors, autologous cells, bone marrow, anti-adhesion agents, anti-cancer agents, or gene and DNA constructs.

In use, the dural graft 10 can be placed in contact with bodily tissue for use as an adhesion barrier, for short-term body contact for moisture retention, or for tissue protection or repair. When used as an implant, the dural graft 10 can be resorbed by the body in a range of about 8 months and 12 months time. In one embodiment, the dural graft 10 can be utilized during a surgical procedure to repair or replace damaged meningeal membranes.

Figure 5:
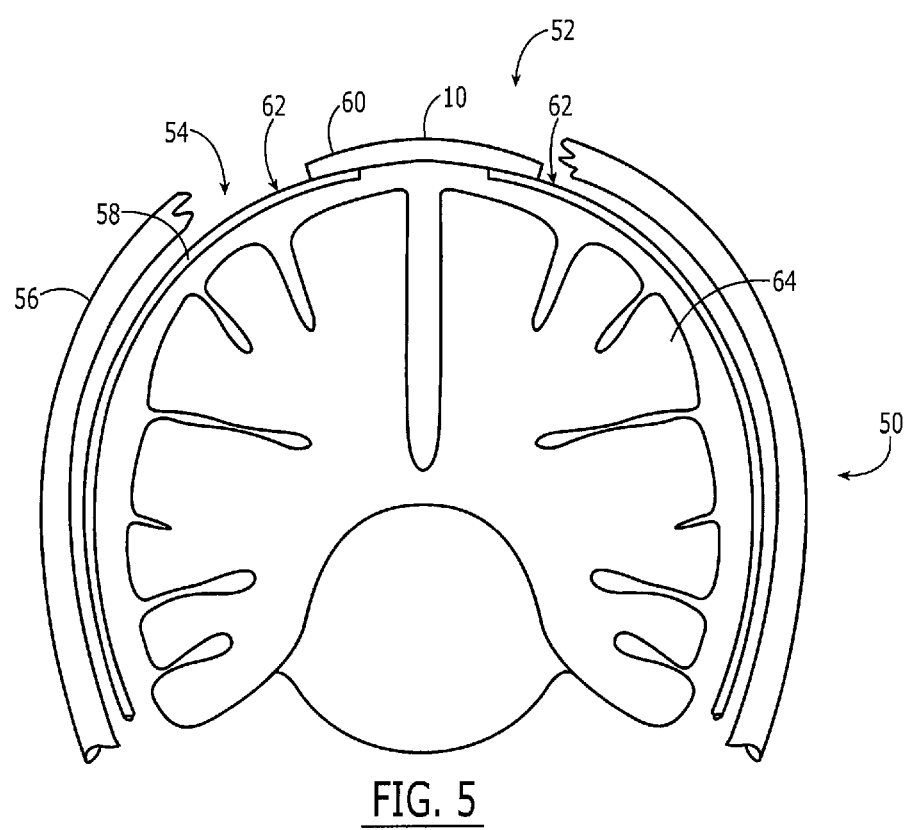
FIG. 5 is a sectional view of a portion of a cranium having the dural graft of FIG. 1 implanted therein.

For example, FIG. 5 illustrates a portion of a cranium 50 having a damaged dura mater site 52. During implantation, the dural graft 10 is inserted through an opening 54 of the skull 56 of the cranium 50 and is placed in contact with a meningeal membrane 58 at the site 52. For example, the dural graft 10 is placed at the site 52 such that an edge 60 of the dural graft 10 overlaps a portion of the meningeal membrane 58 and contacts a non-damaged portion of the dura mater 62. With the dural graft 10 having a relatively small stiffness and a relatively large amount of flexibility, the dural graft 10 can be manipulated or maneuvered during implantation at the site 52 with minimal, if any, tearing of the graft 10.

As the dural graft 10 contacts the dura mater 62, the dural graft 10 substantially conforms to a general curvature of the meningeal membrane 58. For example, as shown in FIG. 5, the dural graft 10 forms a curved shape substantially similar to a curvature of the meningeal membrane 58. With the dural graft 10 having a reduced stiffness and an increased of pliability, the dural graft 10 can sufficiently conform to the curved surface of a meningeal membrane 58. The conformance of the dural graft 10 minimizes the presence of gaps between the dural graft 10 and the meningeal membrane 58 thereby allowing the dural graft 10 to substantially contain cerebrospinal fluid (CSF) within the brain 132 after implantation of the graft 10.

In one embodiment, the conformability of the dural graft 10 relative to the meningeal membrane 58 allows the dural graft 10 to be used as an onlay graft. As such, sutures would not be required to secure the dural graft 10 to the meningeal membrane 58. Instead, the weight of the dural graft 10 maintains the relative positioning of the dural graft 10 relative to the site 52. In another embodiment, however, the dural graft 10 can be secured to the meningeal membrane 58 using sutures.

The dural graft 10 has been shown as a single layer sheet. In one embodiment, the dural graft 10 can be used as a component of a multi-layer sheet, such as illustrated in FIGS. 6 and 7.

Figure 6:
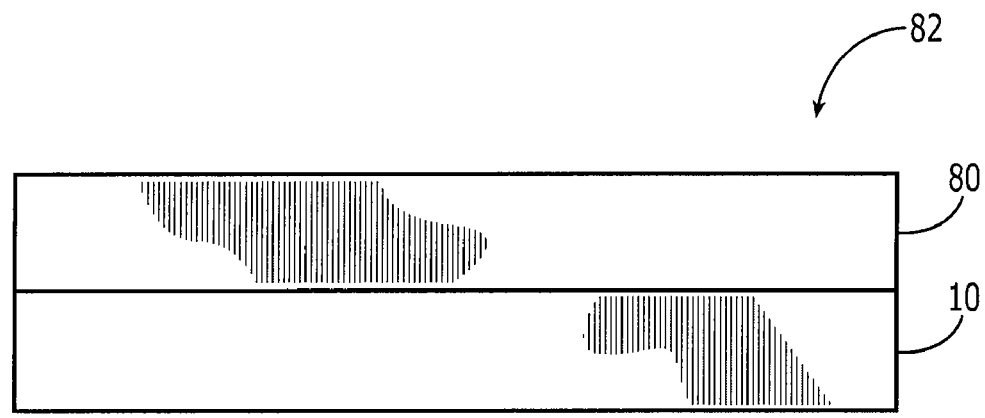
FIG. 6 illustrates a side view of a multi-layer dural graft material that includes the dural graft of FIG. 1.
Figure 7:
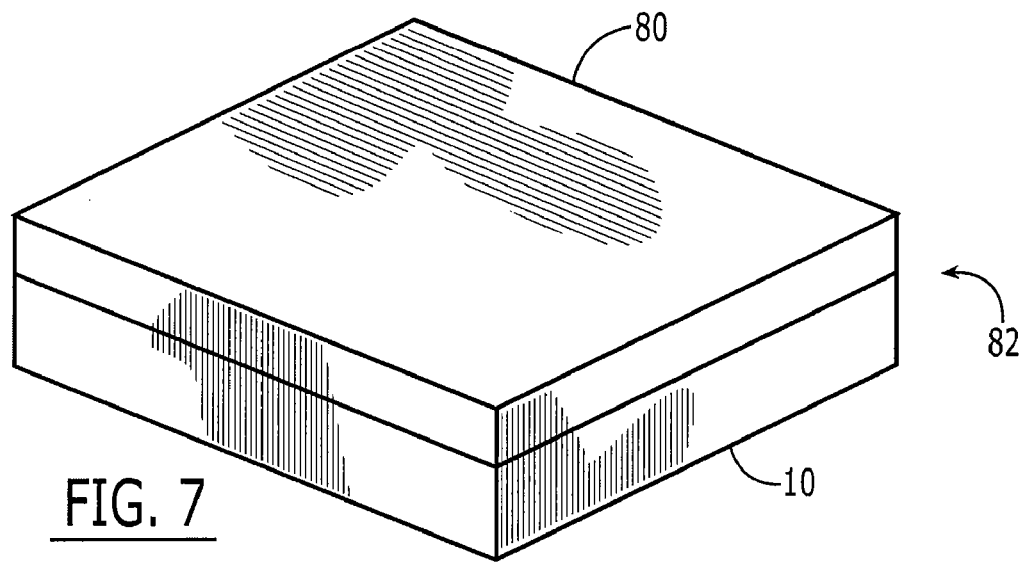
FIG. 7 illustrates a perspective view of the multi-layer dural graft material of FIG. 6.

In one embodiment, as shown in FIGS. 6 and 7, the dural graft 10 can be combined with a collagen sheet 80 to form a dural graft material 82. The dural graft 10 is configured to augment or improve one or a number of characteristics of the collagen sheet 80 such as fluid impermeability or handling characteristics of the collagen sheet 80. For example, as indicated above, conventional collagen sheets are formed from a porous, sponge-like structure that are not fluid impervious. When used in combination with the collagen sheet 80, the dural graft 10 can provide a level of fluid impermeability to the collagen sheet 80 as part of the dural graft material 82.

As shown in FIGS. 6 and 7, the dural graft 10 is positioned adjacent to the collagen sheet 80. In one embodiment, the surface tension of a body fluid (e.g., cerebral spinal fluid) in contact with the dural graft material 82 maintains contact between the dural graft 10 and the collagen sheet 80 during implantation. In another embodiment, the dural graft 10 and the collagen sheet 80 can be physically joined together after implantation. For example, sutures can be applied to the dural graft material 82 to attach the dural graft material 82 to a meningeal membrane and to physically couple the dural graft 10 and the collagen sheet 80.

With respect to FIGS. 6 and 7, while the dural graft material 82 is shown as having a single dural graft layer 10 and a single collagen sheet layer 80 one skilled in the art will appreciate that the dural graft material 82 can be configured in any number of ways. For example, in one embodiment, the dural graft material 82 can include a dural graft 10 disposed between two collagen sheet layers 80. In another embodiment, the dural graft material 82 can include a collagen sheet layer 80 disposed between two dural graft layers 10.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for manufacturing a dural graft substitute, comprising:
    delivering energy to a collagen material at a power level and for a period of time sufficient to reduce a stiffness of the collagen material to a stiffness in a range of about 0.01 pounds per inch to 0.25 pounds per inch.

2. The method of claim 1, comprising reducing the stiffness of the collagen material to a stiffness in a range of about 0.04 pounds per inch to 0.12 pounds per inch.

3. The method of claim 1, wherein the energy is microwave energy.

4. The method of claim 3, wherein delivering microwave energy comprises delivering microwave energy to the collagen material at a power of in a range of about 50 Watts to 1200 Watts for a duration in the range of about of about 5 second to 180 seconds.

5. The method of claim 3, wherein delivering microwave energy comprises delivering microwave energy to the collagen material at a power of in a range of about 200 Watts to 800 Watts for a duration in the range of about of about 15 second to 60 seconds.

* * * * *